(12) United States Patent
Xu

(10) Patent No.: US 8,502,015 B1
(45) Date of Patent: Aug. 6, 2013

(54) METHOD OF INDUCING CANCER

(75) Inventor: Weidong Xu, Tampa, FL (US)

(73) Assignee: Transgenex Nanobiotech, Inc.

( * ) Notice: Subject to any disclaimer, the term of this patent is extended or adjusted under 35 U.S.C. 154(b) by 173 days.

(21) Appl. No.: 12/831,129

(22) Filed: Jul. 6, 2010

Related U.S. Application Data

(60) Provisional application No. 61/223,307, filed on Jul. 6, 2009.

(51) Int. Cl.
*A01K 67/00* (2006.01)
*C12N 15/00* (2006.01)

(52) U.S. Cl.
USPC ................................................ 800/8; 800/21

(58) Field of Classification Search
USPC ....................................................... 800/8, 21
See application file for complete search history.

(56) References Cited

U.S. PATENT DOCUMENTS

| | | |
|---|---|---|
| 6,489,458 B2 | 12/2002 | Hackett et al. |
| 2008/0293055 A1 | 11/2008 | Freeman et al. |

OTHER PUBLICATIONS

Fusco et al. (Mol. cell Biol. (1987) pp. 3365-3370).*
Bos (Cancer Research (1989) vol. 49, pp. 4682-4689).*
Lengyel, E. Review: Ovarian Cancer Development and Metastasis. The American Journal of Pathology (2010), vol. 177(3), pp. 1053-1064.*
Marc T. Goodman et al., Stage at Diagnosis of Ovarian Cancer in the United States, 1992-1997, North American Association of Central Cancer Registries, copyright 2003 American Cancer Society, p. 2648-2659, 12 pages.
Mukesh Kumar et al., Intranasal Gene Transfer by Chitosan-DNA Nanospheres Protects BALB/c Mice Against Acute Respiratory Syncytial Virus Infection, Human Gene Therapy 13:1415-1425 (Aug. 10, 2002), copyright Mary Ann Liebert, Inc., 11 pages.
Chang Won Park et al., DNA methylation of Sleeping Beauty with transposition into the mouse genome, Genes to Cells (2005) 10, 763-776, copyright Blackwell Publishing Limited, 14 pages.
Aron M. Geurts et al., Gene Transfer into Genomes of Human Cells by the Sleeping Beauty Transposon System, Molecular Therapy vol. 8, No. 1, Jul. 2003, copyright the American Society of Gene Therapy, p. 108-117, 10 pages.
Cui Z et al., Structure-function analysis of the inverted terminal repeats of the sleeping beauty transposon, J Mol Biol. May 2002 17;318(5), abstract only, 2 pages.
Yoshiro Hori et al., Two-phase CT Pulmonary Angiography for Detection of Hilar Pulmonary Thromboembolism, Radiation Medicine: vol. 23 No. 6, 414-417 p.p., 2005, 4 pages.
Marc T. Goodman Ph.D., M.P.H. et al., Descriptive epidemiology of Ovarian cancer in the United States, 1992-1997, copyright 2003 American Cancer Society, 14 pages.
Margit Maria Janat-Amsbury et al., Comparison of ID8 MOSE and VEGF-modified ID8 Cell Lines in an Immunocompetent Animal Model for Human Ovarian Cancer, Anticancer Research 26: 2785-2790 (2006), 5 pages.
Barbara C Vanderhyden et al., Animal models of ovarian cancer, Reproductive Biology and Endocrinology 2003, 1:67, copyright 2003 Vanderhyden et al., 11 pages.
T. N. Fredrickson, Ovarian Tumors of the Hen, Environmental Health Perspectives vol. 73, pp. 35-51, 1987, 17 pages.
K. D. Sloan Stakleff et al., Rodent models for ovarian cancer research, Int J Gynecol Cancer 2003, 13, 405-412, 8 pages.
Zoltan Ivics, et al., Molecular Reconstruction of Sleeping Beauty, a Tc1-like Transposon from Fish, and Its Transposition in Human Cells, Cell, vol. 91, 501-510, Nov. 14, 1997, copyright 1997 by Cell Press, 10 pages.
Margaret Sullivan Pepe et al., Phases of Biomarker Development for Early Detection of Cancer, JNCI J Natl Cancer Inst (2001) 93 (14): 1054-1061, 18 pages.
Christine H. Holschneider, MD et al., Ovarian Cancer: Epidemiology, Biology, and Prognostic Factors, Seminars in Surgical Oncology 2000; 19:2-10, 8 pages.

* cited by examiner

*Primary Examiner* — Jon E Angell
(74) *Attorney, Agent, or Firm* — Paradies Law P.A.; Christopher Paradies

(57) ABSTRACT

A method induces cancer, such as ovarian cancer, in primates for testing of therapeutic treatments and preclinical research and development. A nanoparticle delivers plasmid DNA encoding oncogenes and siRNAs for tumor suppressor genes. For example, a biocompatible polymer, chitosan, is complexed with three plasmids including one that carries the cDNA encoding RAS oncogene and two plasmids encoding siRNAs for two tumor supressor genes p53 and Rb. Laproscopic delivery of these nanoparticles to the ovaries of nonhuman primates causes ovarian carcinoma, which is detected one month after delivery of the nanoparticles.

17 Claims, 15 Drawing Sheets

Fig. 1 Construcion of pSB11.

Fig. 5

```
1   GCTGGAGCTC ACCGCGGTGG CGGCCGGCTCT AGAACTAGTG GATCCCCCGG GCTGCAGGAA
61  TTCAAGACTC CAGTGGTAAT CTACTCTCTT GAAGTAGATT ACCACTGGAG TCGGGCCCAA
121 ACAAGGCTTT TCTCCAAGGG ATATTTATAG TCTCAAAACA CACAATTACT TTACAGTTAG
181 GGTGAGTTTC CTTTGTGCT GTTTTTAAA ATAATAATT AGTATTTGTA TCTCTTATAG
241 AATCCAAGC CTATCATGTA AAATGTAGCT AGTATTAAAA AGAACAGATT ATCTGTCTTT
301 TATCGCACAT TAAGCCTCTA TAGTTACTAG GAAATATTAT ATGCAAATTA ACCGGGGCAG
361 GGGAGTAGCC GAGCTTCTCC CACAAGTCTG TGCGAGGGGG CCGGCGCGGG CCTAGAGATG
421 GCGGCGTCGG ATCCACTAGT TCTAGAGCGG GTACCCAATT CGCCCTATAG TGAGTCGTAT
481 TACGCGCGCT CACTGGCCGT CGTTTTACAA CGTCGTGACT GGGAAAACCC TGGCGTTACC
541 CAACTTAATC GCCTTGCAGC ACATCCCCCT TTCGCCAGCT GGCGTAATAG CGAAGAGGCC
601 CGCACCGATC GCCCTTCCCA ACAGTTGCGC AGCCTGAATG GCGAATGGGA CGCGCCCTGT
661 AGCGGCGCAT TAAGCGCGGC GGGTGTGGTG GTTACGCGCA GCGTGACCGC TACACTTGCC
721 AGCGCCCTAG CGCCCGCTCC TTTCGCTTTC TTCCCTTCCT TTCTCGCCAC GTTCGCCGGC
781 TTTCCCCGTC AAGCTCTAAA TCGGGGGCTC CCTTTAGGGT TCCGATTTAG TGCTTTACGG
841 CACCTCGACC CCAAAAAACT TGATTAGGGT GATGGTTCAC GTAGTGGGCC ATCGCCCTGA
901 TAGACGGTTT TTCGCCCTTT GACGTTGGAG TCCACGTTCT
```

The sequence of the vector-driven sip53 was confirmed by sequencing. The following sequence is the exact sequencing data we got form our Molecular Core facility. The siRNA sequences are in bold face and separated by a 8-bp loop.

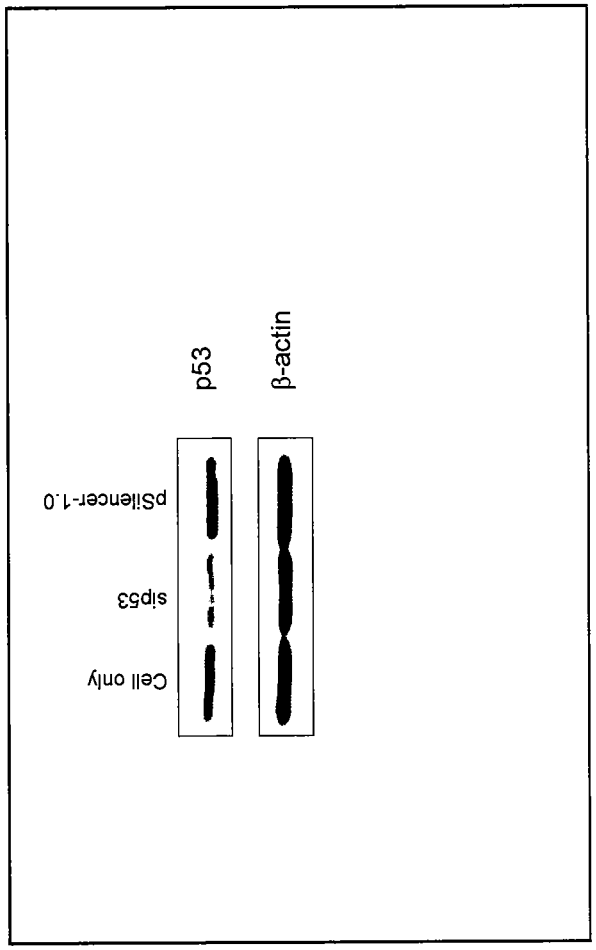
Fig. 6. Expression of p53 reduced by siRNA for p53. HEK293 cells were transfected with sip53 plasmid or control plasmid pSilencer-1.0. p53 levels were detected by Western blot. Mock, cells without transfection; sip53, cells transfected with siRNA for p53; pSilencer-4.0, cells transfected with control plasmid pSilencer-4.0. Expression of β-actin was included as internal control.

two primers by including *Apa*I recognition site (gggccc in green) and *Eco*RI recognition site (gaattc, purple). The exact primer sequences are:

Top strand:
5'-CATATGgggcccGGAGAAAGTTTCATCTGTGGActacgtacTCCACAGATGAAACTTTCTCCTTgaattcCCATGG-3'

Bottom strand:
5'-CCATGGgaattcAAGGAGAAAGTTTCATCTGTGGAgtacgtagTCCACAGATGAAACTTTCTCCgggcccCATATG-3'

```
                          c   t        c
GGAGAAAGTTTCATCTGTGGA          a
|||||||||||||||||||||          
TTCCTCTTTCAAAGTAGACACCT c  a  t        g
```

Fig. 7

CMV promoter: bases 137-724
T7 promoter/priming site: bases 664-683
Multiple cloning site: bases 696-811
BGH reverse priming site: bases 823-840
BGH polyadenylation signal: bases 829-1053
Kanamycin resistance gene: bases 1226-2020
pUC origin: bases 2320-2993

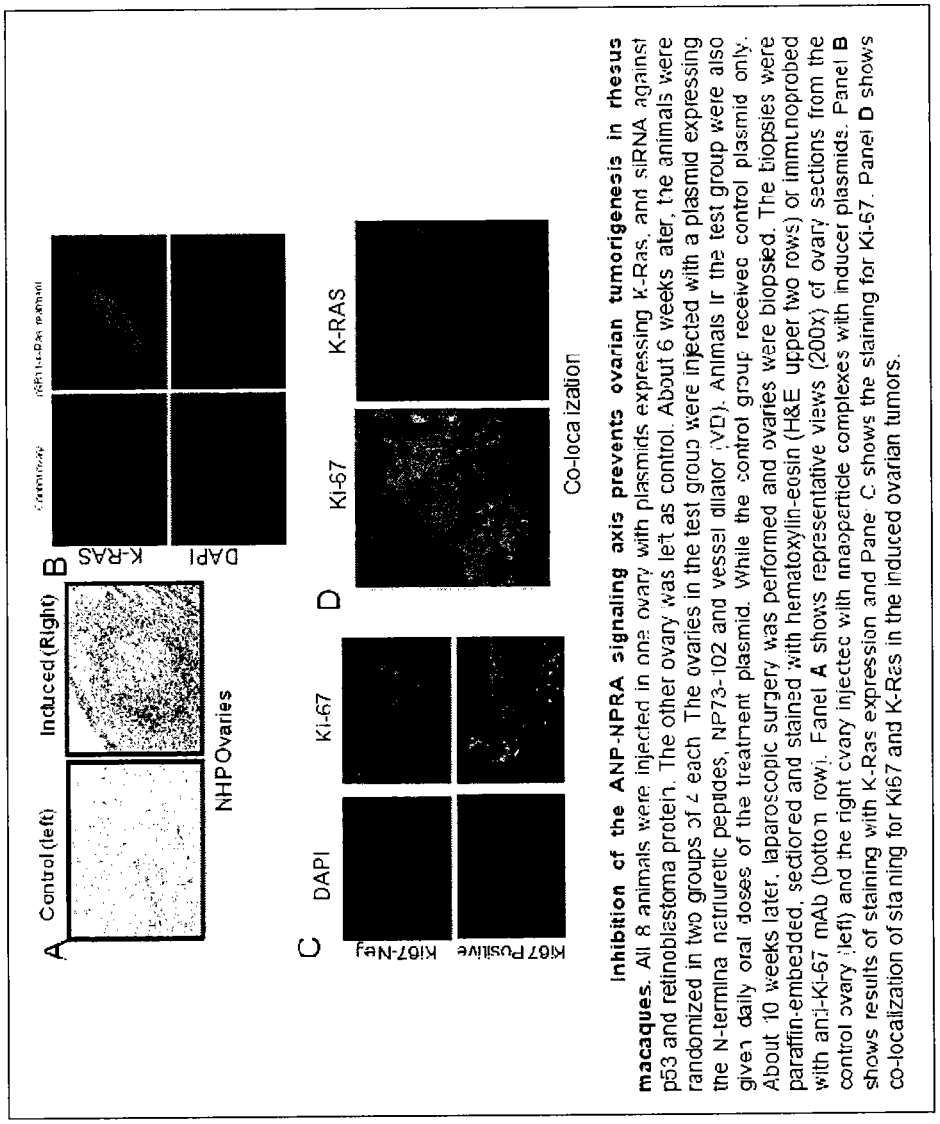

Fig. 9

Inhibition of the ANP-NPRA signaling axis prevents ovarian tumorigenesis in rhesus macaques. All 8 animals were injected in one ovary with plasmids expressing K-Ras, and siRNA against p53 and retinoblastoma protein. The other ovary was left as control. About 6 weeks ater, the animals were randomized in two groups of 4 each. The ovaries in the test group were injected with a plasmid expressing the N-termina natriuretic peptides, NP73-102 and vessel dilator (VD). Animals in the test group were also given daily oral doses of the treatment plasmid. While the control group received control plasmid only. About 10 weeks later, laparoscopic surgery was performed and ovaries were biopsied. The biopsies were paraffin-embedded, sectioned and stained with hematoxylin-eosin (H&E upper two rows) or immunoprobed with anti-Ki-67 mAb (bottom row). Panel A shows representative views (200x) of ovary sections from the control ovary (left) and the right ovary injected with nanoparticle complexes with inducer plasmids. Panel B shows results of staining with K-Ras expression and Pane C shows the staining for Ki-67. Panel D shows co-localization of staining for Ki67 and K-Ras in the induced ovarian tumors.

Inhibition of ovarian tumor growth, as seen by tumor sizes by NP73-102 nanoparticles.

Fig. 11 Inhibition of ovarian tumor growth by NP73-102 nanoparticles.; Top: tumor sizesBottom: tumor weight Fig. 12 Comparison of tumor size and weight among groups treated with nanoparticles complexed with different constructs.

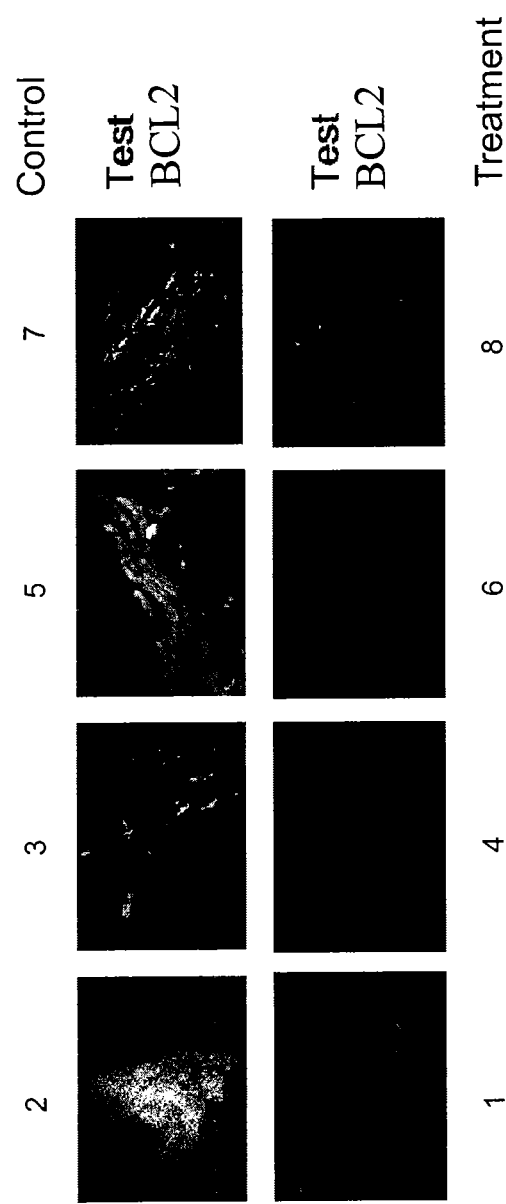

METHOD OF INDUCING CANCER

RELATED APPLICATION

This application claims the benefit of the filing date of U.S. Provisional Patent Application No. 61/223,307 filed Jul. 6, 2009, the disclosure of which is hereby incorporated herein by reference in its entirety.

SEQUENCE LISTING

A compact disk including the sequence listing of SEQ. ID NOS. 1-8 is incorporated by reference herein. A copy of the sequence listings is available in electronic form from the USPTO upon request.

FIELD OF THE INVENTION

The field relates to methods of inducing cancer in primates for the purpose of testing safety and therapeutic effectiveness of biotechnology and pharmaceutical treatment of cancer.

BACKGROUND

Ovarian cancer is a serious threat and ranks among the top leading causes of cancer deaths among women in the United States. It affects 1 in 58 women living in the U.S. It is estimated that 20,180 women will be diagnosed with ovarian cancer in 2006 and approximately 15,310 women will die of the disease (www.ovariancancer.org). Survival rates are low when the diagnosis is in the advanced stages. Ninety five percent of women diagnosed with advanced stage disease will survive no longer than 5 years. The standard of treatment for patients with advanced-stage ovarian cancer in the last decade has been surgery followed by platinum-based chemotherapy. Although 80% of the patients who are treated with this regimen initially show improvement, the cancer recurs in a majority of them. Patients with advanced ovarian cancer who do not respond to initial therapy or those with recurrent disease are severely limited in therapeutic options. Identification of safer and more effective treatments is a critical need for these patients. For example, one potential improvement in treatment might be the delivery of therapeutic agents directly to the abdominal cavity since it directs treatment to the site of the tumor. Gene transfer into genomes of human cells has been shown using the Sherping Beauty transposon system derived from teleost fish sequence as taught, for example, in Geurts et al., *Molecular Therapy*, Vol. 8, No. 1, July 2003, pp. 108-117, which is incorporated herein in its entirety, by reference. Ivics et al., *Cell*, Vol. 91, Nov. 14, 1997, pp. 501-510, teaches the amino acid sequence of SB10, SEQ. ID. NO. 1, for example; which is incorporated herein in its entirety by reference. The sequence listings in the references incorporated by reference herein are now and are likewise incorporated herein.

The lack of specific symptoms, the relative inaccessibility of the ovaries deep in the pelvis, and the absence of specific marker(s) represent barriers for early detection (Bast R C et al Cancer Treat Res. 2002; 107:61-97; Pepe M S, et al. J Natl Cancer Inst. 2001; 93:1054-1061). In most cases, ovarian cancer is diagnosed at a late stage (Goodman M T et al. Cancer. 2003; 97(Suppl 10): 2648-2659). Furthermore, our understanding of the early pathogenesis of ovarian cancer has been hindered by the lack of sufficient number of patients with early-stage disease (Goodman M T et al. Cancer. 2003; 97(Suppl 10): 2648-2659; Reis L A Cancer. 1993; 71(Suppl 2):524-529; Holschneider C H, Berek J S. Semin Surg Oncol. 2000; 19:3-10). Animal models of human diseases are widely used to address questions of tumor development. Selection of a particular animal model depends upon a variety of factors, among them: animal cost, species lifespan, and hardiness; availability of biomolecular and genetic tools for that species; and evolutionary distance from humans. Animal models are used to elucidate disease etiologies and pathogenesis that are difficult to study in humans. Although large domestic mammals including bovine have similar reproductive traits and develop ovarian cancer spontaneously similar to humans, the low incidence rate, multiple pregnancies, longer gestation, and lactation period make them an inappropriate model for human ovarian cancer. On the other hand, a number of rodent models, induced or genetically manipulated, have been developed and used successfully to elucidate some aspects of ovarian cancer. Chickens (*Gallus domesticus*) also develop spontaneous ovarian cancer with a high incidence rate (Damjanov I. Curr Top Pathol. 1989; 78:1-10; Fredrickson T N. Environ Health Perspect. 1987; 73:35-51). However, the nonspontaneous nature (Stakleff K D, Von Gruenigen V E. Int J Gynecol Cancer. 2003; 13:405-412; Vanderhyden B C, et al Reprod Biol Endocrinol. 2003; 1:67) and the time taken to develop cancers of some of these models and lack of resemblance to human disease limits their clinical relevance. In this study, we have developed a robust method to develop cancers rapidly in non-human primates, which closely resemble to humans and will permit screening of cancer drugs for safety and efficacy.

Ovarian cancer, like all cancers, is associated with genetic mutations and, therefore, gene therapy offers a promising approach for its treatment. However, gene therapy is limited by unacceptable risks from the use of viral vectors and by the lack of a system for targeting anticancer drugs to specific cancer cells. We proposed a gene therapy strategy combining nanotechnology and the Sleeping Beauty transposon-based nonviral gene transfer system (Ivics Z, et al *Cell* 1997, 91(4): 501-510; Geurts A M et al; *Mol Ther* 2003, 8(1):108-117; Cui Z, et al *J Mol Biol* 2002, 318(5):1221-1235) to achieve targeted delivery of DNA-based drugs to cancer cells for treatment of ovarian cancer. See also, U.S. Pat. No. 6,489,458 which is incorporated herein in its entirety. Over the past few years, we have developed modified chitosan particles as platforms for DNA-based therapy. Chitosan, a natural biocompatible cationic polysaccharide extracted from crustacean shells, has good potential for the delivery of genes and drugs, as it combines the ability to protect DNA from nucleases and slow-sustained release of DNA [M Kumar, et al *Hum Gene Ther* 2002, 13:1415-25.1], which is herein incorporated by reference in its entirety.

We have identified a novel natriuretic peptide, NP73-102, as a candidate drug for cancer. First, we investigated if stable expression of NP73-102 mediated by the Sleeping Beauty nanotransposon (SB) [15-17] could protect mice from developing ovarian cancer. We also tested another N-terminal natriuretic peptide, vessel dilator (VD) for anticancer properties in the nude mouse model. Our study showed that both VD and NP73-102 provided protection against ovarian cancer in mouse models. Secondly, we investigated if VD and NP73-102 provided protection against ovarian cancer in non-human primate models. We used novel nanoparticles containing siRNAs for p53 and pRb and mutant K-Ras to induce ovarian tumors in rhesus monkeys and then treat the animals with pSB11-NP73-102/VD nanoparticles. Our nonhuman primate model studies confirmed that Sleeping Beauty-mediated nanotransposon expressing natriuretic peptides protect against ovarian cancer development.

Currently, most of the anti-cancer drug evaluations were carried out by using murine models, such as SKOV3/nude mouse model or ID8/C57BL/6 model. However, humans differ from mice. The Applicant has proposed to evaluate TGN208 in non-human primates, using a Rhesus monkey model, for example. This model is an excellent ovarian cancer model for chemoprevention studies, because Rhesus monkeys have similar ovarian and menstrual systems as humans. It is thought, without being limiting in any way, that results from such primate models will be more relevant in guiding research and development of therapies in humans than less similar models such as mice and chicken.

SUMMARY

A composition and method is effective to cause cancer in non-human primates. The primates may be used to screen and test efficacy of ovarian cancer drugs and therapies. The same method can be used to develop other difficult cancer models such as lung, prostate, breast, pancreas and others. An example of a composition comprises one or more plasmids encoding an oncogene, such as RAS oncogene, and/or inhibitors of tumor suppressor genes such as siRNA inhibiting p53 and Retinoblastoma (Rb) gene. The following provides some examples of compositions and methods for inducing cancer in primates.

BRIEF DESCRIPTION OF THE DRAWINGS

FIG. 5 shows sequencing confirmation of sip53, SEQ. ID. NO. 6, cloned in plasmid pSilencer-4.0-sip53, SEQ. ID. NO. 2. The siRNA sequences are in bold face and separated by a 8-bp loop.

FIG. 6 shows Expression of p53 reduced by siRNA for p53. HEK293 cells were transfected with sip53 plasmid or control plasmid pSilencer-1.0. p53 levels were detected by Western blot. Mock, cells without transfection; sip53 cells transfected with siRNA for p53; pSilencer-4.0 cells transfected with control plasmid pSilencer-4.0. Expression of β-actin was included as internal control.

FIG. 7 shows predicted structure of siRb. There is a 8-bp loop in the middle and a TT-overhang at the 3'-end.

FIG. 9 shows the development of an ovarian cancer model in rhesus monkeys by using nanogene transfer. All eight animals were injected in one ovary with plasmids expressing K-Ras, and siRNA against p53 and retinoblastoma protein. The other ovary was left as control. About six weeks later, the animals were randomized in two groups of four each. The ovaries in the test group were injected with a plasmid expressing the N-terminal natriuretic peptides, NP73-102 and vessel dilator (VD). Animals in the test group were also given daily oral doses of the treatment plasmid. While the control group received control plasmid only. About 10 weeks later, laparoscopic surgery was performed and ovaries were biopsied. The biopsies were paraffin-embedded, sectioned and stained with hematoxylin-eosin (H&E, upper two rows) or immunoprobed with anti-Ki-67 mAb (bottom row). Panel A shows representative views (200×) of ovary sections from the control ovary (left) and the right ovary injected with nanoparticle complexes with inducer plasmids. Panel B shows results of staining with K-Ras expression and Panel C shows the staining for Ki-67. Panel D shows co-localization of staining for Ki67 and K-Ras in the induced ovarian tumors.

FIG. 15 shows inhibition of the ANP-NPRA signaling axis prevents ovarian tumorigenesis in rhesus macaques. All eight animals were injected in one ovary with plasmids expressing K-Ras, and siRNA against p53 and retinoblastoma protein. The other ovary was left as control. About 6 weeks later, the animals were randomized in two groups of four each. The ovaries in the test group were injected with a plasmid expressing the C-terminal natriuretic peptides, NP73-102 and vessel dilator (VD) while the control group received plasmid only. Animals in the test group were also given daily oral doses of the plasmid. About 10 weeks later, laparoscopic surgery was performed and ovaries were biopsied. The biopsies were paraffin-embedded, sectioned and immunoprobed with anti-Bcl2 mAb.

DETAILED DESCRIPTION

Example 1

Construction of Sleeping Beauty Transposon Vector pSB11

SB transposase contains 340 amino acids. Its N-terminal 123 amino acids are the DNA-binding domain, which specifically interacts with SB IR/DR sequences. There are several typical domains indentified in the enzyme, such as the NLS domain, glycine-rich box and a DD(34)E catalytic domain. Mutagenesis of the SB10 transposase revealed that several amino acid substitutions created an improved transposase called SB11, which has 3-4 fold higher activity than the SB10 transposase.

At first, we constructed a transposon expression vector, pSB10. We did codon optimization of the SB transposase SB10 to clone pSB10. SB10 encodes 340 amino acids and its gene has 1020 base pairs. The optimized SB10 gene is listed below (from ATG to TAA, in bold font), SEQ. ID. NO. 1. The restriction enzyme NheI site and XbaI site were introduced at the 5' end and 3' end, respectively, so that the SB10-optimized gene could be cloned into pVAX1 vector.

To generate an SB10-optimized gene fragment, a total of 29 oligonucleotide primers were synthesized. Among these primers, four were PCR primers (SB-PCRFW, SB5-RV, SB5-FW, SB-PCRRV); 13 top strand primers (SB1 to SB13, 80-bp each), 12 bottom strand primers (SB14 to SB25, 40-bp each). The optimized SB10 gene was cloned in pVAX1, which was previously digested with NheI and XbaI double. By using the same techniques, we also amplified DNA fragments of SB left IR/DR, right IR/DR. The final expression vector pSB10 was constructed in three steps. The first step is to clone the left IR/DR at a unique MluI site in pVAX1; then to clone the right IR/DR fragment at a KasI site; and the last step is to amplify optimized SB10 with a CMV promoter and BGH poly A sequence using pVAX1-SB10 as template; BspHI sites were introduced in the PCR primer and finally then SB10 optimized gene was inserted at the unique BspHI site of the recombinant pVAX1 plasmids which has left IR/DR and right IR/DR cloned.

Figure 1:
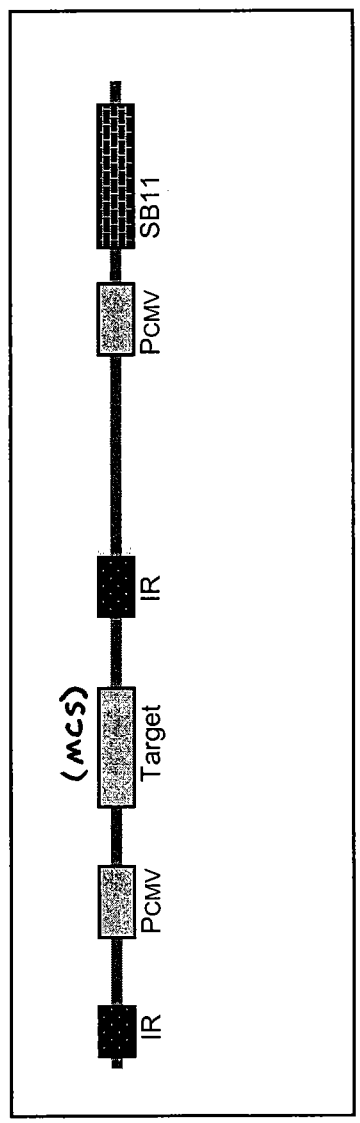
FIG. 1 shows the construction of pSB11 vector. Target genes can be inserted at the multiple cloning site (MCS).

The version of Sleeping Beauty transposon vector, pSB11, was finally constructed by replacing SB10 with SB11. SB11, SEQ. ID. NO. 7, has four amino acid residues mutated, the activity of SB11 is 3-4 folds higher than that of SB10 (FIG. 1).

Example 2

Figure 2:
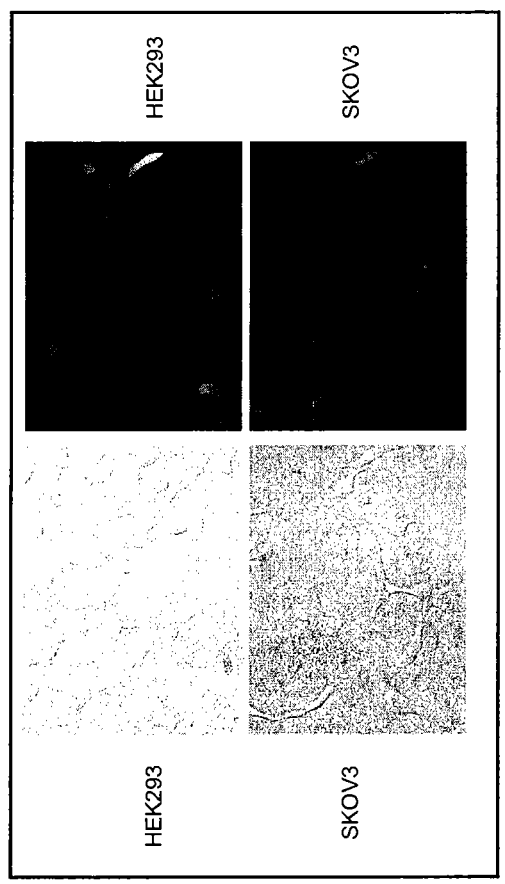
FIG. 2 shows the stable expression of GFP mediated by Sleeping Beauty transposon pSB11. HEK 293 and SKOV3 cells were observed under fluorescent microscope in regular (left panel) and fluorescent light (right panel) 79 days after transfection.

Stable Expression of GFP Reporter Protein by Mediation of Sleeping Beauty Transposon Target genes can be cloned into the MCS in pSB11. We first tested the stability of SB-mediated GFP expression in ovarian cancer cells. In the plasmid pSB11-EGFP, the reporter GFP gene was cloned under CMV promoter. When HEK293 or SKOV3 cells were transfected with pSB11-EGFP, the integration of GFP gene into the chromosome could be mediated by Sleeping Beauty transposon. Without any selection, GFP expression is still stable in ovarian cancer SKOV3 cells even on day 79 after transfection (FIG. 2).

Example 3

Construction of pSB11-K-Ras

Figure 3:
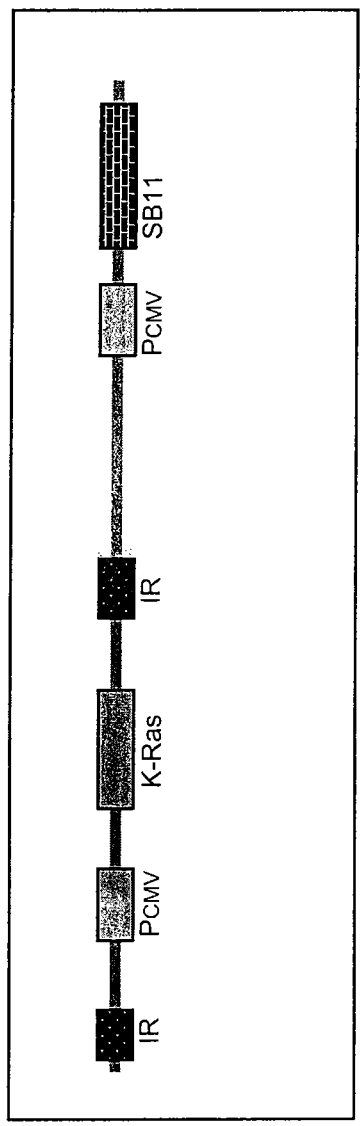
FIG. 3 shows construction of pSB11-K-Ras. K-Ras gene fragment was amplified by PCR and then inserted at the MCS in pSB11.

In order to induce ovarian cancer tumors in rhesus monkeys, we use pSB11 and constructed a vector, which could stably express oncogene K-Ras, SEQ. ID. NO 5. K-Ras gene was PCR amplified and then cloned between the NheI and NotI sites in pSB11. pSB11-K-Ras was purified and then mixed with two vector-driven siRNAs for p53 and pRb to develop tumor-inducing nanoparticles. The structure of pSB11-K-Ras is shown in FIG. 3.

Example 4

Construction of siRNAs for p53 and pRb

In order to induce ovarian cancer tumors in rhesus monkeys, we cloned siRNA for p53, SEQ. ID. NO. 6 in pSilencer-4.0 resulting in psilencer 4.0-sip53, SEQ. ID. NO. 2, to knock out p53 as shown in FIG. 5. Sip53 may be cloned in the plasmid pSilencer-4.1-CMV-puro (FIG. 4) SEQ. ID. NO. 8, also. The sequence of the vector-driven sip53 was confirmed by sequencing. As shown in FIG. 5, the siRNA sequences for p53, SEQ. ID. NO. 6, are in bold face and separated by a 8-bp loop.

We tested the efficacy of sip53 to reduce p53 expression at cell levels. HEK293 cells grown on 60-mm plates were transfected with 1 μg of pSilencer-4.0-sip53 plasmid DNA, SEQ. ID. NO. 2, and the control vector pSilencer-4.0, without sip53, respectively. Forty-eight hours later, the transfected cells were detached from the plates and washed twice with PBS. The whole cell protein of the transfected cells were prepared with standard methods and then subjected to Western blot assay to quantify the expression of p53 using primary antibodies against p53 (Cell Signaling Technology, MA). Cells without transfection were also included as mock control. In FIG. 6, the expression of p53 decreases significantly compared to mock control and control vector pSilencer-4.0 without sip53.

Figure 4:
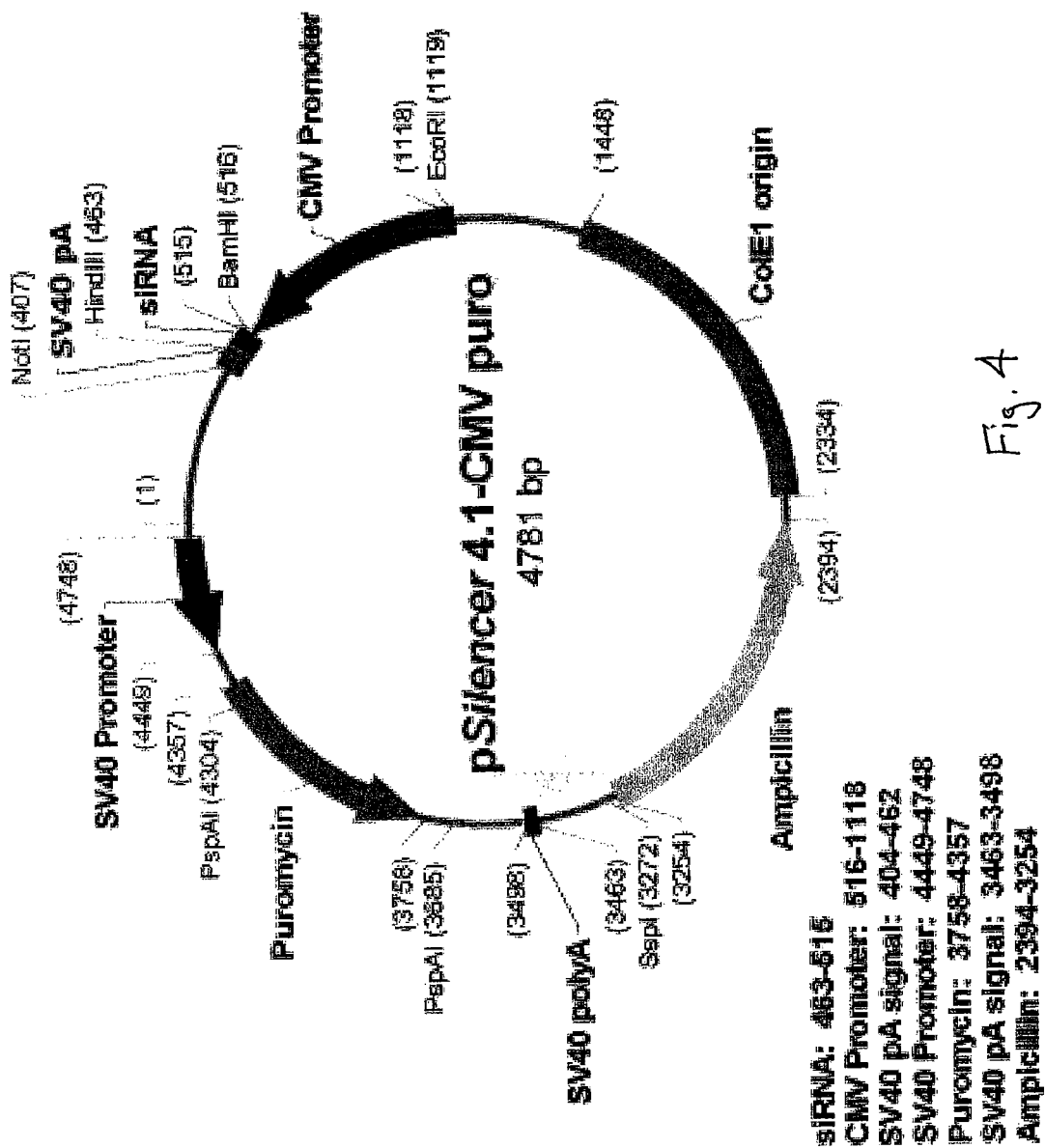
FIG. 4 shows physical map of pSilencer 4.1-CMV, SEQ. ID. NO. 8.

Similarly, we cloned siRNA for pRb to knock out pRb in order to induce ovarian cancer in rhesus monkeys. The target sequence of Rb used to design siRb is GGAGAAAGTTTCATCTGTGGA, SEQ. ID. NO. 3, which is at position of 232 nt in pRb mRNA. After the two primers are boiled at 100° C. for 5 min, they are annealed and then digested by ApaI and EcoRI before being cloned between ApaI and EcoRI of pSilencer-4.1-CMV (Ambion, Tex.), SEQ. ID. NO. 8, which was previously treated by these two retraction enzymes As illustrated in FIG. 4. FIG. 7 illustrates the predicted structure of siRb produced in cells, SEQ. ID. NO. 4.

We confirmed siRNA for pRB to reduce pRb expression by Western blot assay. HEK293 cells grown on 6-cm plates were transfected with 1.5 μg of pSilencer-4.1-siRb and control plasmid pSilencer-1.0, respectively. The transfected cells were harvested and the whole protein was extracted according to standard procedure. Cells without transfection were also included as mock control. Equal amount of proteins from different treatment were separated by SDS-PAGE, transferred to PVDF membranes, and then probed with primary antibodies against human pRb (Cell Signaling Technology, MA). Expression of pRb was significantly lower in HEK293 cells after transfection with siRb. Therefore, the siRNA for pRb we designed is effective in silencing pRb expression.

Example 5

Development of an Ovarian Cancer Model in Rhesus Monkeys by Using Nanogene Transfer A major stumbling block for drug development against ovarian cancer is the lack of good animal model. TransGenex Nanobiotech Inc has developed a rhesus monkey model using chitosan nanoparticle mediated gene transfers. First, to develop ovarian cancer, eight monkeys were injected with nanoparticles containing plasmid mixture of sipRb, SEQ. ID. NO 3, sip53, SEQ. ID. NO. 6 and K-Ras, SEQ. ID. NO 5. The nanoparticles were delivered to right ovary laparoscopically. The left ovary served as control. After 2 months, all monkeys had developed ovarian carcinoma in the right ovary as seen immunohistology of biopsy sections (FIG. 9A). The H & E staining of biopsies collected from ovaries during laparoscopy showed that monkeys given the inducer treatment induced ovarian tumors (FIG. A). Both K-Ras and Ki-67 were also overexpressed in monkeys that developed tumors by nanoparticle—pSB11-KRas at early stage. Ki-67 and KRas expressions were significantly lower in control ovaries, as shown in FIGS. 9B-C. Tumor sections were stained for cancer biomarkers of Ki-67 and K-Ras. Expression of both Ki-67 and KRas were obvious in the tumors as shown in FIG. 9D. Finally, comparisons were made between monkeys, which received the NPRA inhibitor treatment (pSB11-NP73-102/

VD plasmid), and control (received vector only). Comparison of total staining of ovary sections showed that the treated monkeys had substantially reduced or close to no staining of K-Ras, Ki-67 and p53-neg compared to control monkeys (n=4). Overall, these studies have shown the significance of ANP-NPRA signaling pathways for ovarian cancer in this nonhuman primate model.

Example 6

Antitumor Activities of NP73-102 in Ovarian Cancer Nude Mouse Model

Figure 8:
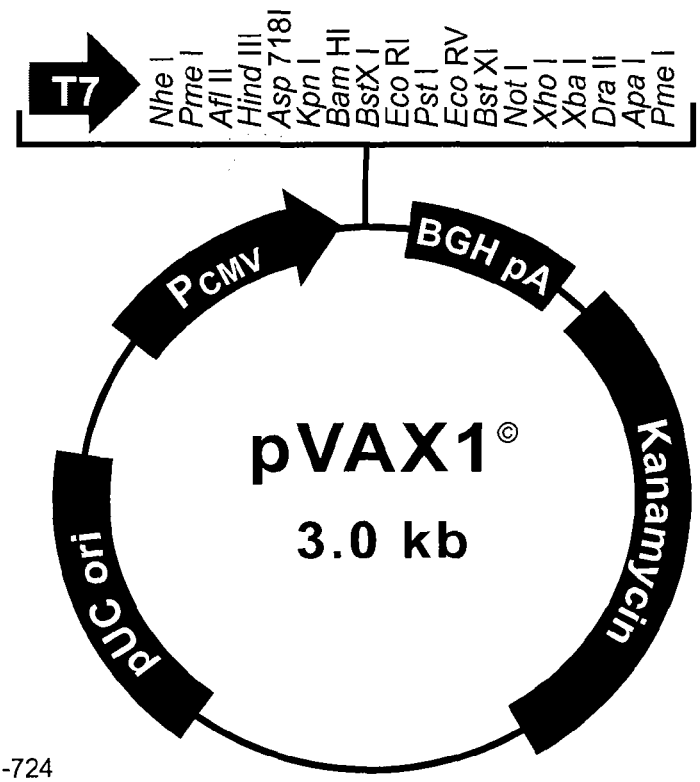
FIG. 8 illustrates physical map of pVax1.
Figure 10:
FIG. 10 shows inhibition of ovarian tumor growth, as seen by tumor sizes, by NP73-102 nanoparticles.
Figure 11:
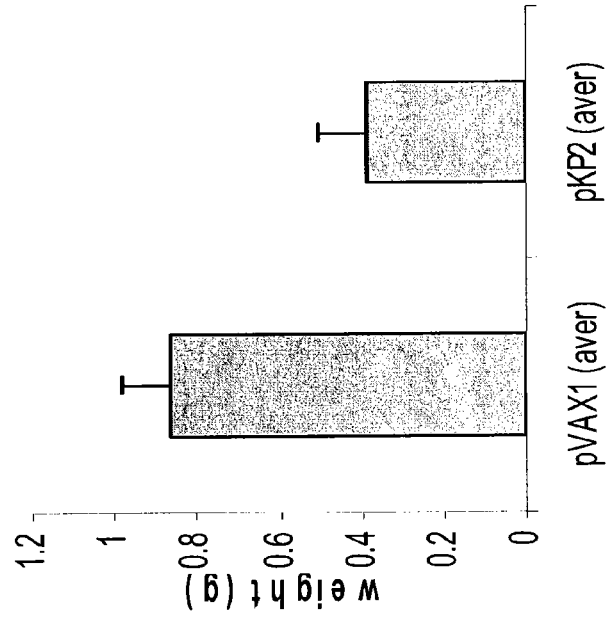
FIG. 11 shows the inhibition of ovarian tumor growth, as seen by weight, by NP73-102 nanoparticles.

NP73-102 gene fragment was amplified and cloned into pVAX1 (FIG. 8). Eight Balb/c nude mice were injected subcutaneously in the right flank with 5 million ovarian cancer (SKOV3) cells. The animals were then divided into 2 groups (n=4 per group) and were injected i.p. with 25 µg of pVAX1-NP73-102 and pVAX1 control plasmid, respectively. Each animal was treated once a week with the same plasmid. Tumor formation was monitored for about eight weeks, and all mice were sacrificed. The tumors were removed and weighed. The difference of tumor size and tumor weight was illustrated in FIGS. 10 and 11.

Example 7

Antitumor Activities of VD Chitosan Nanoparticles

Figure 12:
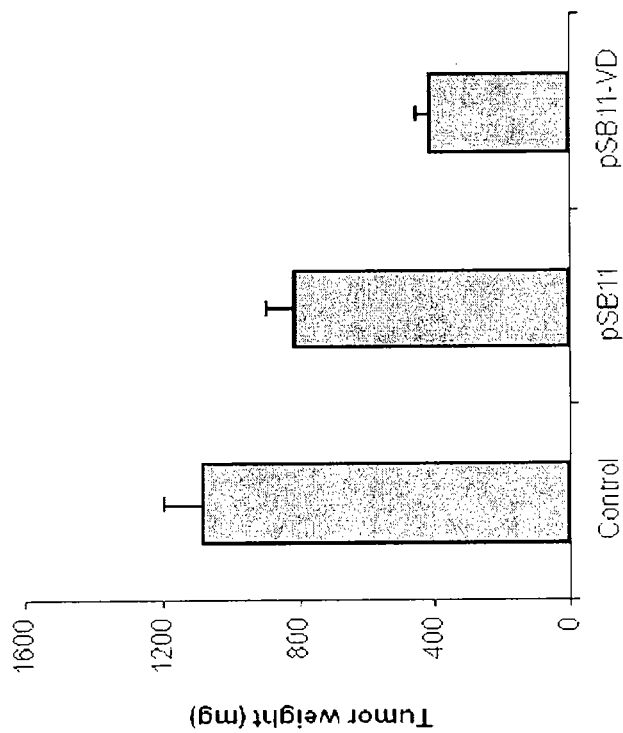
FIG. 12 shows inhibition of ovarian tumor growth, as seen by weight, by pSB11-VD nanoparticles
Figure 13:
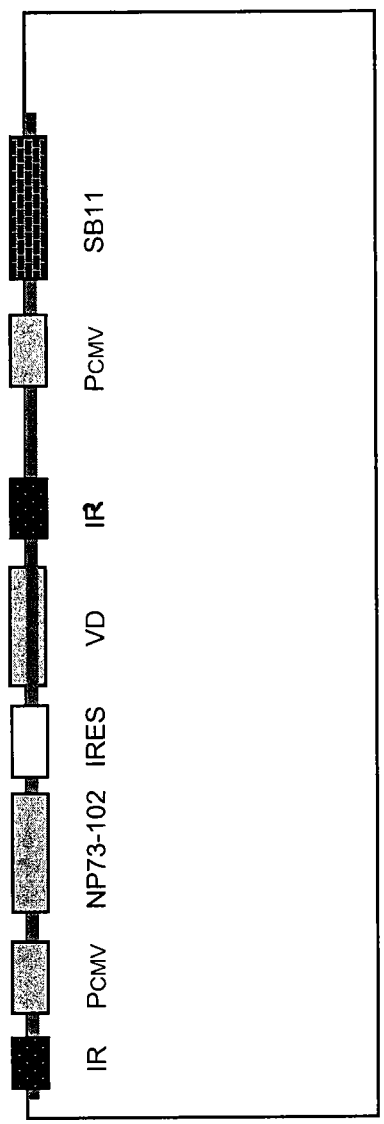
FIG. 13 shows the construction of pSB11-VD. VD gene fragment was amplified by PCR and then inserted at the MCS in pSB11.

VD gene fragment was amplified by PCR and then cloned into pSB11 (FIG. 13). Twelve C57BL/6 mice were subcutaneously injected with 5 million of spontaneous ovarian cancer ID8/VEGF cells (Janat-Amsbury M M, Anticancer Res. 2006, 26:2785-9). All animals were then divided into three groups (n=4 each group): The control group received no treatment; the pSB11 control group were injected i.p. with 25 µg of pSB11 chitosan nanoparticles; the treatment group were injected i.p. with 25 µg of pSB11-VD chitosan nanoparticles. Each animal was treated once a week with the same plasmid. Tumor formation was monitored for about 10 weeks, and all mice were sacrificed. The difference of tumor weight was illustrated in FIG. 12.

Example 8

Construction of pSB11-NP73-102/VD

We constructed a vector, which could express both NP73-102 and VD expecting to improve the antitumor activity of the nanomedicine we proposed. The vector is named pSB11-KP2/VD, in which the expression of both NP73-102 and VD are controlled by a single CMV promoter, but separated by an internal ribosome entry site (IRES) of hepatitis C virus. The mediation of IRES allows the simultaneous expression of both NP73-102 and VD. There are two steps in the cloning strategy. Since there are two different multiple cloning sites (MCS) in the original cloning vector, pIRES (purchased from Clontech), mouse NP731-02 gene was subcloned between the NheI and XhoI sites in MCS1. The next step is to clone VD gene between the XbaI and NotI sites in MCS2 in pKP2-IRES. VD gene fragment (about 160 bp) was PCR amplified from pro-ANP cDNA. Since XbaI site and NotI recognition sequences were both introduced in two different PCR primers, respectively, the PCR-amplified VD fragment was digested with XbaI and NotI before subcloning into the MCS2 of pKP2-IRES. To clone pSB11-KP2/VD, KP2/VD gene fragment was removed from pKP2-IRES-VD and then inserted between NheI and NotI sites in pSB11-CMV (FIG. 13). In the new recombinant plasmid pSB11-NP73-102/VD, both VD and NP73-102 (KP2) genes are expressed from the same plasmid under the control of CMV promoter and with the advantage of stable gene integration and expression through the modified Sleeping Beauty transposon SB11. We have confirmed and isolated this new plasmid in large scale using Qiagen's endotoxin-free plasmid purification Giga kit.

Example 9

TGN208 Protect Rhesus Monkeys from Developing Ovarian Cancer

Figure 14:
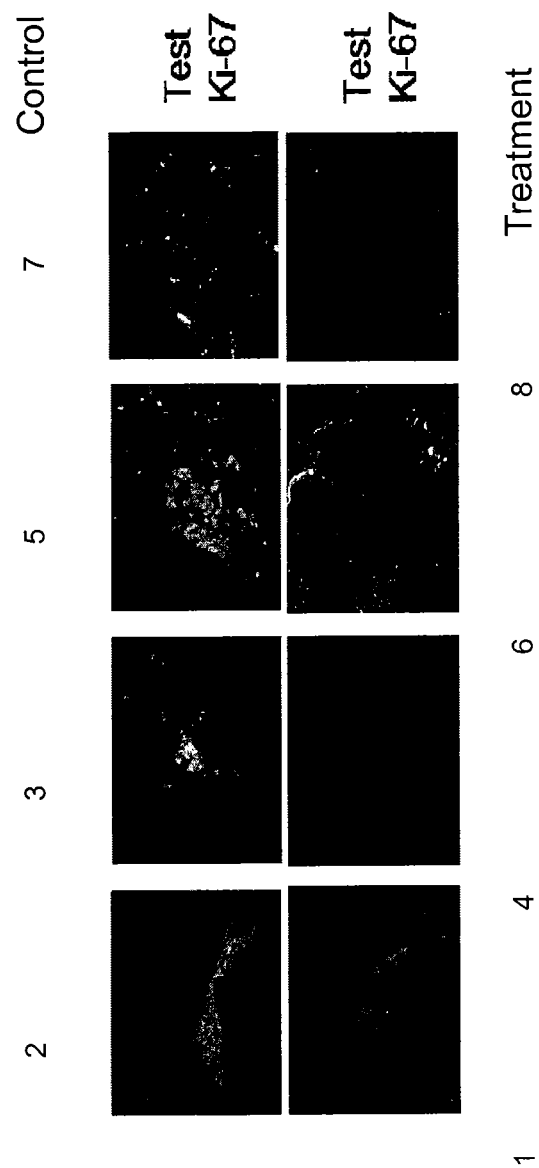
FIG. 14 inhibition of the ANP-NPRA signaling axis prevents ovarian tumorigenesis in rhesus macaques. All eight animals were injected in one ovary with plasmids expressing K-Ras, and siRNA against p53 and retinoblastoma protein. The other ovary was left as control. About 6 weeks later, the animals were randomized in two groups of four each. The ovaries in the test group were injected with a plasmid expressing the C-terminal natriuretic peptides, NP73-102 and vessel dilator (VD) while the control group received plasmid only. Animals in the test group were also given daily oral doses of the plasmid. About 10 weeks later, laparoscopic surgery was performed and ovaries were biopsied. The biopsies were paraffin-embedded, sectioned and immunoprobed with anti-Ki-67 mAb.

The anticancer efficacy of our nanomedicine TGN208 (pSB11-KP2/VD chitosan nanoparticles) has been evaluated in eight rhesus monkeys by measuring the expression level of tumor proliferative indices, Ki-67 antigen, K-Ras and Bcl2, in the ovary sections. Ovary tissues were biopsied during laparoscopy and fixed with paraformaldehyde. Tissue fragments were centrifuged and washed 3× with PBS, and permeabilized by 20 min treatment with 0.2% triton X-100. An aliquot was incubated 4 hr at RT with mouse monoclonal antibody to human ki-67 nuclear proliferation factor or Bcl2. After washing 3× with PBS, the tissue was incubated 1 hr at RT with FITC-conjugated donkey anti-mouse IgG. The stained tissue was applied to a slide, mixed with a drop of mounting medium containing DAPI and cover-slipped. Green fluorescence was observed with an Olympus fluorescence microscope and representative fields were photographed with camera. Ki-67 was overexpressed in three out of four monkeys from the control group (shown in the FIG. 14). Ki-67 expressions were low or negative in all monkeys in the treatment group. In the mean time, staining for BCL2 indicated that all ovaries from the control group showed strong expression, but no expression in the animals treated by TGN208 (FIG. 15). From these results, we may conclude that TGN208 is efficient in protecting against ovarian cancer development.

What is claimed is:

1. A non-human animal model for use in screening and efficacy of cancer therapies in humans, comprising a non-human primate, wherein the non-human primate is treated to induce cancer in tissue of the non-human primate by injecting the tissue of the non-human primate with three tumor-inducing plasmids: a complementary DNA (cDNA) encoding K-RAS oncogene, an siRNA for p53, and an siRNA for Rb.

2. The non-human animal model of claim 1, wherein the tissue is ovarian tissue of a first ovary, while the ovarian tissue of a second ovary of the non-human primate remains as a control.

3. The non-human animal model of claim 1, wherein the cDNA encoding K-RAS oncogene comprises pSB11-K-Ras.

4. The non-human animal model of claim 3, wherein the siRNA for p53 comprises pSilencer4.1-sip53.

5. The non-human animal model of claim 4, wherein the siRNA for Rb comprises pSilencer4.1-sipRb.

6. The non-human animal model of claim 1, wherein the non-human primate is selected as a Rhesus monkey.

7. A process for inducing a tumor in a non-human animal model, comprising injecting tissue of a non-human primate with three tumor-inducing plasmids: a complementary DNA (cDNA) encoding K-RAS oncogene, an siRNA for p53, and an siRNA for Rb.

8. The process of claim 7, wherein the tissue injected in the step of injecting is selected to be ovarian tissue of a first ovary, while the ovarian tissue of a second ovary of the non-human animal model remains as a control.

9. The process of claim 7, further comprising complexing the tumor-inducing plasmids with a chitosan nanoparticle prior to the step of injecting.

10. The process of claim 9, wherein the tissue injected in the step of injecting is ovarian tissue of a first ovary, while the ovarian tissue of a second ovary of the non-human animal model remains as a control.

11. The process of claim 7, further comprising preparing pSB11-K-Ras as the cDNA encoding the K-RAS oncogene.

12. The process of claim 7, further comprising preparing pSilencer4.1-sip53 as the siRNA for p53.

13. The process of claim 7, further comprising preparing pSilencer4.1-sipRB as the siRNA for Rb.

14. The process of claim 13, further comprising preparing pSilencer4.1-sip53 as the siRNA for p53.

15. The process of claim 14, further comprising preparing pSB11-K-Ras as the cDNA encoding the K-RAS oncogene.

16. The process of claim 7, further comprising selecting a non-human primate as the non-human animal model in the step of injecting.

17. The process of claim 7, wherein the non-human primate is selected to be a Rhesus monkey.

\* \* \* \* \*

SEQUENCE LISTING

```
<160> NUMBER OF SEQ ID NOS: 8

<210> SEQ ID NO 1
<211> LENGTH: 340
<212> TYPE: PRT
<213> ORGANISM: Artificial Sequence
<220> FEATURE:
<223> OTHER INFORMATION: SB10 Sleeping Beauty Transposase

<400> SEQUENCE: 1
```

```
Met Gly Lys Ser Lys Glu Ile Ser Gln Asp Leu Arg Lys Lys Ile Val
1               5                   10                  15

Asp Leu His Lys Ser Gly Ser Leu Gly Ala Ile Ser Lys Arg Leu
            20                  25                  30

Lys Val Pro Arg Ser Ser Val Gln Thr Ile Val Arg Lys Tyr Lys His
            35                  40                  45

His Gly Thr Thr Gln Pro Ser Tyr Arg Ser Gly Arg Arg Val Leu
50                      55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
                100                 105                 110

Lys Gly Arg Ser Ala Arg Lys Lys Pro Leu Leu Gln Asn Arg His Lys
            115                 120                 125

Lys Ala Arg Leu Arg Phe Ala Thr Ala His Gly Asp Lys Asp Arg Thr
130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
            195                 200                 205

Ile Asp Gly Ile Met Arg Lys Glu Asn Tyr Val Asp Ile Leu Lys Gln
210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
            275                 280                 285

Val Arg Ala Arg Arg Pro Thr Asn Leu Thr Gln Leu His Gln Leu Cys
290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340

<210> SEQ ID NO 2
<211> LENGTH: 940
<212> TYPE: DNA
<213> ORGANISM: Homo sapiens

<400> SEQUENCE: 2
gctggagctc accgcggtgg cggccgctct agaactagtg atccccggg gctgcaggaa      60 ttcaagactc cagtggtaat ctactctctt gaagtagatt accactggag tcgggcccaa     120
acaaggcttt tctccaaggg atatttatag tctcaaaaca cacaattact ttacagttag    180
```

```
ggtgagtttc cttttgtgct gttttttaaa ataataattt agtatttgta tctcttatag    240
aaatccaagc ctatcatgta aaatgtagct agtattaaaa agaacagatt atctgtcttt    300
tatcgcacat taagcctcta tagttactag gaaatattat atgcaaatta accggggcag    360
gggagtagcc gagcttctcc cacaagtctg tgcgaggggg ccggcgcggg cctagagatg    420
gcggcgtcgg atccactagt tctagagcgg gtacccaatt cgccctatag tgagtcgtat    480
tacgcgcgct cactggccgt cgttttacaa cgtcgtgact gggaaaaccc tggcgttacc    540
caacttaatc gccttgcagc acatccccct ttcgccagct ggcgtaatag cgaagaggcc    600
cgcaccgatc gcccttccca acagttgcgc agcctgaatg gcgaatggga cgcgccctgt    660
agcggcgcat taagcgcggc gggtgtggtg gttacgcgca gcgtgaccgc tacacttgcc    720
agcgccctag cgcccgctcc tttcgctttc ttcccttcct ttctcgccac gttcgccggc    780
tttccccgtc aagctctaaa tcggggggctc cctttagggt tccgatttag tgctttacgg    840
cacctcgacc ccaaaaaact tgattagggt gatggttcac gtagtgggcc atcgccctga    900
tagacggttt ttcgcccttt gacgttggag tccacgttct    940
```

```
<210> SEQ ID NO 3
<211> LENGTH: 21
<212> TYPE: DNA
<213> ORGANISM: Homo sapiens

<400> SEQUENCE: 3
ggagaaagtt tcatctgtgg a                                              21

<210> SEQ ID NO 4
<211> LENGTH: 52
<212> TYPE: DNA
<213> ORGANISM: Homo sapiens

<400> SEQUENCE: 4
ggagaaagtt tcatctgtgg actacgtact ccacagatga aactttctcc tt            52

<210> SEQ ID NO 5
<211> LENGTH: 567
<212> TYPE: DNA
<213> ORGANISM: Homo sapiens

<400> SEQUENCE: 5
atgactgaat ataaacttgt ggtagttgga gctgttggcg taggcaagag tgccttgacg     60
atacagctaa ttcagaatca ttttgtggac gaatatgatc caacaataga ggattcctac    120
aggaagcaag tagtaattga tggagaaacc tgtctcttgg atattctcga cacagcaggt    180
caagaggagt acagtgcaat gagggaccag tacatgagga ctggggaggg ctttctttgt    240
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag ggtgttgatg atgccttcta tacattagtt    480
cgagaaattc gaaaacataa agaaaagatg agcaaagatg gtaaaaagaa gaaaaagaag    540
tcaaagacaa agtgtgtaat tatgtaa                                        567

<210> SEQ ID NO 6
<211> LENGTH: 47
<212> TYPE: DNA
<213> ORGANISM: Homo sapiens
```

<400> SEQUENCE: 6

```
gactccagtg gtaatctact ctcttgaagt agattaccac tggagtc          47
```

<210> SEQ ID NO 7
<211> LENGTH: 1023
<212> TYPE: DNA
<213> ORGANISM: Artificial Sequence
<220> FEATURE:
<223> OTHER INFORMATION: SB11 Sleeping Beauty Transposase

<400> SEQUENCE: 7

```
atgggaaaat caaaagaaat cagccaagac ctcagaaaaa aaattgtaga cctccacaag    60
tctggttcat ccttgggagc aatttccaaa cgcctgaaag taccacgttc atctgtacaa   120
acaatagtac gcaagtataa acaccatggg accacgcagc cgtcataccg ctcaggaagg   180
agacgcgttc tgtctcctag agatgaacgt actttggtgc gaaaagtgca aatcaatccc   240
agaacaacag caaaggacct tgtgaagatg ctggaggaaa caggtacaaa agtatctata   300
tccacagtaa aacgagtcct atatcgacat aacctgaaag gccgctcagc aaggaagaag   360
ccactgctcc aaaaccgaca taagaaagcc agactacggt tgcaagagc  atgggggac   420
aaagatcgta cttttttggag aaatgtcctc tggtctgatg aaacaaaaat agaactgttt   480
ggccataatg accatcgtta tgtttggagg aagaagggg  aggcttgcaa gccgaagaac   540
accatcccaa ccgtgaagca cggggggtggc agcatcatgt tgtgggggtg ctttgctgca   600
ggagggactg tgcacttca  caaaatagat ggcatcatga ggaaggaaaa ttatgtggat   660
atattgaagc aacatctcaa gacatcagtc aggaagttaa agcttggtcg caaatgggtc   720
ttccaacaag acaatgaccc caagcatact tccaaacacg tgagaaaatg gcttaaggac   780
aacaaagtca aggtattgga gtggccatca caaagccctg acctcaatcc tatagaaaat   840
ttgtgggcag aactgaaaaa gcgtgtgcga gcaaggaggc ctacaaacct gactcagtta   900
caccagctct gtcaggagga atgggccaaa attcacccaa cttattgtgg gaagcttgtg   960
gaaggctacc cgaaacgttt gacccaagtt aaacaattta aaggcaatgc taccaaatac  1020
tag                                                                 1023
```

<210> SEQ ID NO 8
<211> LENGTH: 4781
<212> TYPE: DNA
<213> ORGANISM: Artificial Sequence
<220> FEATURE:
<223> OTHER INFORMATION: pSilencer-4.1-CMV puro vector

<400> SEQUENCE: 8

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgccaa gctagcggcc gcatacaaaa   420
aaccaacaca cagatccaat gaaaataaaa gatcctttat taagcttact accgttgtta   480
taggtgtctc ttgaacacct ataacaacgg tagtggatcc acggttcact aaaccagctc   540
tgcttatata gacctcccac cgtacacgcc taccgcccat ttgcgtcaat ggggcggagt   600
```

```
tgttacgaca ttttggaaag tcccgttgat tttggtgcca aaacaaactc ccattgacgt      660
caatggggtg gagacttgga atccccgtg  agtcaaaccg ctatccacgc ccattgatgt      720
actgccaaaa ccgcatcacc atggtaatag cgatgactaa tacgtagatg tactgccaag      780
taggaaagtc ccataaggtc atgtactggg cataatgcca ggcgggccat ttaccgtcat      840
tgacgtcaat aggggcgta  cttggcatat gatacacttg atgtactgcc aagtgggcag      900
tttaccgtaa atactccacc cattgacgtc aatggaaagt ccctattggc gttactatgg      960
gaacatacgt cattattgac gtcaatgggc ggggtcgtt  gggcggtcag ccaggcgggc     1020
catttaccgt aagttatgta acgcggaact ccatatatgg gctatgaact aatgaccccg     1080
taattgatta ctattaataa ctaagatctg gtaccttgaa ttcatgcttc cctccctttt     1140
agtgagggta attctctctc tctccctata gtgagtcgta ttaattcctt ctcttctata     1200
gtgtcaccta atcgttgca  attcgtaatc atgtcatagc tgtttcctgt gtgaaattgt     1260
tatccgctca caattccaca acacatacga gccggaagca taaagtgtaa agcctggggt     1320
gcctaatgag tgagctaact cacattaatt gcgttgcgct cactgcccgc tttccagtcg     1380
ggaaacctgt cgtgccagct gcattaatga atcggccaac gcgcggggag aggcggtttg     1440
cgtattgggc gctcttccgc ttcctcgctc actgactcgc tgcgctcggt cgttcggctg     1500
cggcgagcgg tatcagctca ctcaaaggcg gtaatacggt tatccacaga atcaggggat     1560
aacgcaggaa agaacatgtg agcaaaaggc cagcaaaagg ccaggaaccg taaaaaggcc     1620
gcgttgctgg cgtttttcca taggctccgc cccctgacg  agcatcacaa aaatcgacgc     1680
tcaagtcaga ggtggcgaaa cccgacagga ctataaagat accaggcgtt ccccctggaa     1740
agctccctcg tgcgctctcc tgttccgacc ctgccgctta ccggatacct gtccgccttt     1800
ctcccttcgg gaagcgtggc gctttctcat agctcacgct gtaggtatct cagttcggtg     1860
taggtcgttc gctccaagct gggctgtgtg cacgaaccc  ccgttcagcc cgaccgctgc     1920
gccttatccg gtaactatcg tcttgagtcc aacccggtaa gacacgactt atcgccactg     1980
gcagcagcca ctggtaacag gattagcaga gcgaggtatg taggcggtgc tacagagttc     2040
ttgaagtggt ggcctaacta cggctacact agaagaacag tatttggtat ctgcgctctg     2100
ctgaagccag ttaccttcgg aaaaagagtt ggtagctctt gatccggcaa aaaaccacc      2160 gctggtagcg gtggtttttt tgtttgcaag cagcagatta cgcgcagaaa aaaggatct      2220 caagaagatc ctttgatctt ttctacgggg tctgacgctc agtggaacga aaactcacgt     2280
taagggattt tggtcatgag attatcaaaa aggatcttca cctagatcct tttaaattaa     2340
aaatgaagtt ttaaatcaat ctaaagtata tatgagtaaa cttggtctga cagttaccaa     2400
tgcttaatca gtgaggcacc tatctcagcg atctgtctat ttcgttcatc catagttgcc     2460 tgactcccg  tcgtgtagat aactacgata cgggagggct taccatctgg ccccagtgct     2520
gcaatgatac cgcgagaccc acgctcaccg gctccagatt tatcagcaat aaaccagcca     2580
gccggaaggg ccgagcgcag aagtggtcct gcaactttat ccgcctccat ccagtctatt     2640
aattgttgcc gggaagctag agtaagtagt tcgccagtta atagtttgcg caacgttgtt     2700
gccattgcta caggcatcgt ggtgtcacgc tcgtcgtttg gtatggcttc attcagctcc     2760
ggttcccaac gatcaaggcg agttacatga tcccccatgt tgtgcaaaaa agcggttagc     2820
tccttcggtc ctccgatcgt tgtcagaagt aagttggccg cagtgttatc actcatggtt     2880
atggcagcac tgcataattc tcttactgtc atgccatccg taagatgctt ttctgtgact     2940
ggtgagtact caaccaagtc attctgagaa tagtgtatgc ggcgaccgag ttgctcttgc     3000
```

-continued

```
ccggcgtcaa tacgggataa taccgcgcca catagcagaa ctttaaaagt gctcatcatt    3060
ggaaaacgtt cttcggggcg aaaactctca aggatcttac cgctgttgag atccagttcg    3120
atgtaaccca ctcgtgcacc caactgatct tcagcatctt ttactttcac cagcgtttct    3180
gggtgagcaa aaacaggaag gcaaaatgcc gcaaaaaagg gaataagggc gacacggaaa    3240
tgttgaatac tcatactctt cctttttcaa tattattgaa gcatttatca gggttattgt    3300
ctcatgagcg gatacatatt tgaatgtatt tagaaaaata aacaaatagg ggttccgcgc    3360
acatttcccc gaaaagtgcc acctgacgtc taagaaacca ttattatcat gacattaacc    3420
tataaaaata ggcgtatcac gagattgcag tgaaaaaaat gctttatttg tgaaatttgt    3480
gatgctattg ctttatttgt aaccattata agctgcaata aacaagttaa caacaacaat    3540
tgcattcatt ttatgtttca ggttcagggg gaggtgtggg aggtttttta aagcaagtaa    3600
aacctctaca aatgtggtat ggctgattat gatcctctag agtcggtggg cctcggggc    3660
gggtgcgggg tcggcgggc cgccccgggt ggcttcggtc ggagccatgg ggtcgtgcgc    3720
tcctttcggt cgggcgctgc gggtcgtggg gcgggcgtca ggcaccgggc ttgcgggtca    3780
tgcaccaggt gcgcggtcct tcgggcacct cgacgtcggc ggtgacggtg aagccgagcc    3840
gctcgtagaa ggggaggttg cggggcgcgg aggtctccag gaaggcgggc accccggcgc    3900
gctcggccgc ctccactccg gggagcacga cggcgctgcc cagacccttg ccctggtggt    3960
cgggcgagac gccgacggtg gccaggaacc acgcgggctc cttgggccgg tgcggcgcca    4020
ggaggccttc catctgttgc tgcgcggcca gccgggaacc gctcaactcg gccatgcgcg    4080
ggccgatctc ggcgaacacc gccccgctt cgacgctctc cggcgtggtc cagaccgcca    4140
ccgcggcgcc gtcgtccgcg acccacacct tgccgatgtc gagcccgacg cgcgtgagga    4200
agagttcttg cagctcggtg acccgctcga tgtggcggtc cgggtcgacg gtgtggcgcg    4260
tggcggggta gtcggcgaac gcggcggcga gggtgcgtac ggcccgggg acgtcgtcgc    4320
gggtggcgag gcgcaccgtg ggcttgtact cggtcatgga aggtcgtctc cttgtgaggg    4380
gtcaggggcg tgggtcaggg gatggtggcg gcaccggtcg tggcggccga cctgcaggca    4440
tgcaagctag cttttttgcaa aagcctaggc ctccaaaaaa gcctcctcac tacttctgga    4500
atagctcaga ggccgaggcg gcctcggcct ctgcataaat aaaaaaaatt agtcagccat    4560
ggggcggaga atgggcggaa ctgggcggag ttaggggcgg gatgggcgga gttaggggcg    4620
ggactatggt tgctgactaa ttgagatgca tgctttgcat acttctgcct gctggggagc    4680
ctggggactt tccacacctg gttgctgact aattgagatg catgctttgc atacttctgc    4740
ctgctgggga gcctgggac tttccacacc aatctttcgt c                        4781
```